US009433654B2

(12) United States Patent
Efstathiou et al.

(10) Patent No.: US 9,433,654 B2
(45) Date of Patent: Sep. 6, 2016

(54) COMPOSITIONS CONTAINING BROCCOLI SEEDS FOR TREATMENT OR PREVENTING PROSTATE CANCER

(75) Inventors: Theo Efstathiou, Pace (FR); Nicolas Plu, Domagne (FR)

(73) Assignee: Sojasun Technologies, Noyal sur Vilaine (FR)

( * ) Notice: Subject to any disclaimer, the term of this patent is extended or adjusted under 35 U.S.C. 154(b) by 324 days.

(21) Appl. No.: 14/128,874

(22) PCT Filed: May 29, 2012

(86) PCT No.: PCT/EP2012/060069
§ 371 (c)(1),
(2), (4) Date: Mar. 7, 2014

(87) PCT Pub. No.: WO2013/004436
PCT Pub. Date: Jan. 10, 2013

(65) Prior Publication Data
US 2014/0170218 A1    Jun. 19, 2014

(30) Foreign Application Priority Data

Jul. 1, 2011  (FR) ..................................... 11 55926

(51) Int. Cl.
*A61K 36/31*   (2006.01)
*A23L 1/30*   (2006.01)
*A61K 9/28*   (2006.01)

(52) U.S. Cl.
CPC .............. *A61K 36/31* (2013.01); *A23L 1/3002* (2013.01); *A61K 9/28* (2013.01)

(58) Field of Classification Search
CPC .................................................... A61K 36/31
USPC ........................................................ 424/755
See application file for complete search history.

(56) References Cited

U.S. PATENT DOCUMENTS

| 7,744,937 | B2 * | 6/2010 | West | A23L 1/3002 424/755 |
| 2002/0151505 | A1 * | 10/2002 | Fahey | A23L 1/30 514/23 |
| 2006/0127996 | A1 * | 6/2006 | Fahey | A23L 1/3002 435/128 |
| 2007/0031581 | A1 * | 2/2007 | West | A23L 1/3002 426/655 |
| 2009/0081138 | A1 * | 3/2009 | Ashurst | A61K 36/31 424/59 |
| 2011/0135766 | A1 * | 6/2011 | Wehrli | A61K 36/31 424/755 |
| 2011/0287109 | A1 * | 11/2011 | Bagley | A23L 1/3002 424/638 |
| 2012/0213890 | A1 * | 8/2012 | Sullivan | A23L 1/034 426/61 |

FOREIGN PATENT DOCUMENTS

| FR | 2888235 | * | 1/2007 |
| FR | 28882035 | A1 | 1/2007 |
| WO | 2010023162 | A1 | 3/2010 |

OTHER PUBLICATIONS

The French International Search Report and Written Opinion dated Feb. 17, 2012.
The English translation of the International Search Report dated Aug. 2, 2012.
Kristal, et al., "Brassica Vegetables and Prostate Cancer Risk: A Review of the Epidemiological Evidence," Nutrition and Cancer, London, GB, vol. 42, No. 1, Jan. 1, 2002, pp. 1-9.
Singh, et al., "Sulforaphane Induces Caspase-Mediated Apoptosis in Cultured PC-3 Human Prostate Cancer Cells and Retards Growth of PC-3 Xenografts in Vivo," Carcinogensis, Oxford University Press, vol. 25, No. 1, Jan. 1, 2004, pp. 83-60.
Verhoeven, et al., "Epidemological Studies on Brassita Vegetables and Cancer Risk," Cancer Epidemiology, Biomarkers & Prevention: A Publication of the American Association for Cancer Research, Cosponsored by the American Society of Preventive Oncology, Sep. 1996—vol. 5, No. 9, Sep. 1996, pp. 733-748.
Steinmetz, et al., "Vegetables, Fruit, and Cancer Prevention: A Review," Journal of the American Dietetic Association, Oct. 1996, vol. 96, No. 10, Oct. 1996, pp. 1027-1039.

* cited by examiner

*Primary Examiner* — Chris R Tate
(74) *Attorney, Agent, or Firm* — Thomas|Horstemeyer, LLP

(57) ABSTRACT

The invention relates to a composition for treating or preventing prostate cancer or the recurrence thereof, including a non-aqueous extract of non-germinated broccoli seeds of the *Brassica Oleracea Italica* variety that are rich in sulforaphane. The extract is encapsulated by a compound selected from the group including acacia gum, maltodextrin, and the mixture thereof, and said composition can be provided in the form of a capsule, tablet, sugarcoated tablet, or film-coated tablet, and is orally administered one to three times a day at a daily dose of 2 to 200 mg.

1 Claim, No Drawings ial-scale application of the method for extracting active principles such as glucoraphanin from these seeds. Indeed, the bur-geoning plantlets produce wastes that clog the filter mem-

COMPOSITIONS CONTAINING BROCCOLI SEEDS FOR TREATMENT OR PREVENTING PROSTATE CANCER

CROSS REFERENCE TO RELATED APPLICATION

This application is a continuation-in-part of PCT Application entitled "Compositions Containing Broccoli Seeds for Treatment or Preventing Prostate Cancer," having serial number PCT/EP2012/060069, filed on 29 May 2012, which claims priority to and benefit of French Patent Application No. 1155926, filed on 1 Jul. 2011, both of which are incorporated by reference in their entirety.

FIELD OF THE INVENTION

The field of the invention is that of nutraceutical or pharmaceutical compositions for treating or preventing prostate cancer.

More specifically, the invention pertains to a composition based on broccoli extract for treating or preventing prostate cancer in men.

PRIOR ART

Prostate cancer is the second-largest cause of mortality in Europe and in the United States and generally occurs in individuals aged over 50. There are several forms of this cancer, of which the commonest and most severe form is prostate adenocarcinoma. Highly localized at first, this cancer can spread rapidly to neighboring tissues and form metastases in other tissues (bone, lymph nodes, etc).

The treatment generally applied is total surgical resection of the prostate associated with treatments such as chemotherapy, curietherapy or external radiotherapy. Nevertheless, 30 to 50% of patients show biological recurrence or relapse within ten years of their first treatment. Biological recurrence is the formation of a malignant tumor of a same histological type as the primitive tumor after a first curative treatment. In order to monitor this recurrence, the prostate specific antigen (PSA) level is regularly measured by carrying out serum dosage on the patient.

In addition, the only options offered to the patient in the event of recurrence are:
  simple monitoring, followed by androgen deprivation in the case of rapid development evolution of the illness, or
  premature androgen deprivation.

Androgen deprivation consists of chemical or surgical castration of the patient. Since prostate cancer is a hormone-dependent form of cancer, this radical approach becomes necessary as a last resort. Nevertheless, its efficacy is limited: clones, independent of hormonal stimulation, can appear rapidly. At this stage, the treatment is then reduced to simple palliative care.

Besides, the treatment associated with surgical resection causes many side effects for the patient. Examples of such side effects are nausea, great fatigue, modification of the hemogram, erectile and urinary disorders, digestive disorders, etc.

There is therefore a need for alternatives to prevent or at least limit the onset of recurrence among patients who have undergone operations, in limiting side effects and reducing the discomfort caused by such treatment to the patient.

The consumption of crucifers is known to play a positive role in prostate cancer. The active agent involved is sulforaphane (4-(methylsulfinyl)butyl isothiocyanate), which is a powerful antioxidant known to have a protective role in numerous pathologies: asthma, inflammation of the air passages, cancer of the lung, stomach, colon, rectum, prostate, liver and breast, etc., (Verhoeven et al, Cancer Epidemiol Biomarkers Prev., 1996; Steinmetz et al. J. Am. Diet. Assoc., 1996, Zhang et al. Proc. Natl. Acad. Sci. USA, 1992). Sulforaphane is not present in crucifers as such. It is obtained through enzyme hydrolysis of its precursor, glucoraphanin, through myrosinase which is an enzyme endogenous to crucifers.

The chemopreventive action of sulforaphane is due to its antioxidant properties, which inhibit phase I enzymes (cytochrome P450 enzymes) and activate phase II enzymes (glutathion S transferase for example).

In addition, sulforaphane also has pro-apoptotic activity since it arrests cells in the "G2/M phase", preventing them from entering a mitotic phase and activating the processes of apoptosis. It has been shown that sulforaphane is dose-dependently cytotoxic.

However, it has not yet been brought to the knowledge of the Applicant that compositions have been developed that are aimed at treating or preventing the onset of prostate cancer or its recurrence and that use only extracts of crucifers.

GOALS OF THE INVENTION

The invention is aimed at providing a composition that enables the treatment or prevention of prostate cancer or its recurrence.

It is another goal of the invention, in at least one embodiment, to propose a method for extracting a non-aqueous extract of broccoli seeds that can go into such a composition in order to treat or prevent prostate cancer or its recurrence.

SUMMARY OF THE INVENTION

These goals as well as others that shall appear here below are achieved by means of the invention which pertains to a composition for the treatment or prevention of prostate cancer or its recurrence that comprises, as an active principle and preferably its sole active principle, a non-aqueous extract of non-sprouted broccoli seeds of the *Brassica Oleracea Italica* variety, said extract 10 being rich in sulforaphane and being encapsulated by a compound selected from the group comprising acacia gum, maltodextrin and the mixture thereof, said composition taking the form of a capsule, a tablet, a coated pill or a film-coated tablet and being administered orally one to three times a day, in a dose of 2 to 200 mg/day.

Thus, the invention relies on an innovative approach in which a composition is made to prevent or cure prostate cancer or its recurrence through the use of a non-aqueous extract of one particular variety of broccoli which has proved to be very rich in sulforaphane. The inventors have indeed discovered that non-sprouted seeds of the *Brassica Oleracea Italica* variety of broccoli are particularly rich in glucoraphanin and that it is appropriate to use non-aqueous extracts of these seeds to obtain compositions having optimum efficiency.

It is well known that sprouted seeds are rich in glucoraphanin. In practice, the fact that such seeds have started their sprouting process complicates the industrial-scale application of the method for extracting active principles such as glucoraphanin from these seeds. Indeed, the burgeoning plantlets produce wastes that clog the filter membranes that can be used in the context of such methods. It is then necessary to add additional steps to remove these wastes.

The non-sprouted broccoli seeds, for their part, are known to contain far smaller quantities of active principles such as glucoraphanin than the sprouted seeds and are therefore little used in practice. However, the inventors have discovered that non-sprouted seeds of a particular variety of broccoli, namely *Brassica Oleracea Italica*, have a glucoraphanin content that is high enough for them to be efficiently exploited in order to obtain extracts rich in this active principle.

According to one embodiment of the invention, the compositions according to the invention can be for nutraceutical use and can be administered one to three times a day in a dose ranging from to 2 to 20 mg/day. The term "nutraceutical composition" or "functional food" (also called "pharmafood") is understood to mean a composition based on a food or foods possessing a positive and significant effect on health and on the prevention of pathologies.

The initiation of carcinogenesis corresponds to the mutation of a gene in a cell, induced by an external aggression or an endogenous cause. Forms of external aggression known to provoke carcinogenesis include UV radiation, the consumption of tobacco and alcohol, etc. One of the endogenous causes can be the oxidative stress resulting, for example, from a chronic inflammation. These two mechanisms lead to the formation of free radicals provoking DNA mutation. The regular ingestion of small doses of sulforaphane therefore enables the organism to integrate and potentiate the benefits of sulforaphane, whose antioxidant properties make up for a localized deficit in the DNA repair system (a deficit in glutathion S transferase for example). Through the composition according to the invention, the rise of a carcinogenic mutation is prevented.

Besides, since such compositions have small doses of sulforaphane, it is possible to consume them daily as a nutraceutical without experiencing the cytotoxic effects of sulforaphane. They can therefore be beneficial to adult men who wish to limit their risks of developing a prostate cancer, especially when there is a family context that favors it.

According to another embodiment of the invention, the compositions according to the invention are for pharmaceutical use and can be administered one to three times daily in a dose ranging from 20 to 200 mg/day.

Such compositions can be administered daily to a patient having undergone surgical resection of the prostate following a diagnosis of prostate cancer. These compositions can be administered as a treatment concomitantly with chemotherapy, radiotherapy or curietherapy. They make it possible to reduce the doses of these therapies administered to the patient. This would therefore have the effect of diminishing the negative impact of these medicines on the patient, especially on the liver. This would further reduce the stress and discomfort of the treatment for the patient and his kith and kin.

Such compositions can also be administered between sessions of chemotherapy, curietherapy or radiotherapy. Having no negative effect on the human organism, these compositions are well supported by the patient. At the same time, they protect him efficaciously and they significantly slow down the development of secondary tumors or a recurrence of the cancer.

Yet another object of the invention is a method for obtaining a non-aqueous extract of sulforaphane stabilized by encapsulation for the preparation of a composition according to the invention, the method comprising:

a. a step for mechanical cold pressing of the non-sprouted broccoli seeds of the *Brassica Oleracea Italica* variety leading to a partially dilapidated cake, b. a step of enzyme hydrolysis of said partially dilapidated cake obtained at the step for hydrolyzing the glucoraphanin, contained in said seeds, into sulforaphane, this step leading to the obtaining of a hydrolysate, c. a step for purifying said hydrolysate obtained at the step b by the addition of acetone to reduce the lipid content of said hydrolysate obtained at the step b, as well as its erucic acid content to a concentration below 5% by weight, d. a step for filtering said hydrolysate, enabling the recovery of a filtrate with a low content of lipids and erucic acid, e. a step for evaporating said acetone, contained in said filtrate obtained at the step d, to recover an aqueous phase, f. a step for extracting sulforaphane from said aqueous phase obtained a the step e by the addition of ethyl acetate to recover a phase containing said ethyl acetate and sulforaphane, g. a step for evaporating said ethyl acetate contained in said phase recovered at the step f leading to the obtaining of a non-aqueous extract rich in sulforaphane, containing at least 30% by weight of sulforaphane (this non-aqueous extract takes the form of a viscous product), h. a step for the drying on a polysaccharide support, selected from the group comprising acacia gum, maltodextrin and the mixture thereof, of said non-aqueous extract obtained at the step g leading to the obtaining of a powder, i. a step for increasing the stability of the sulforaphane present in said powder obtained at the step h by encapsulation in a polysaccharide matrix selected from the group comprising acacia gum, maltodextrin and the mixture thereof leading to an encapsulated powder containing at least 10% by weight of sulforaphane, said method being performed without a step of aqueous extraction between the step g and the step h.

It is indeed imperative that the extract obtained should be non-aqueous. In this respect, it can be noted that a method has already been proposed in the prior art for extracting sulforaphane from crucifer seeds, especially broccoli seeds, leading to the obtaining of an aqueous extract. This method described in the patent FR2888235 leads to the obtaining of aqueous extracts, which have proved to be unsuited to the making of compositions according to the invention.

Through the method according to the invention, it is possible to make compositions based on stabilized sulforaphane that can be packaged, commercially distributed and stored for pharmaceutical or nutraceutical use.

Extraction by mechanical pressing enables the elimination of a part of the lipids present in the non-sprouted broccoli seeds. The cake thus obtained contains, among other elements, glucoraphanin and myrosinase, which are endogenous to broccoli. The addition of water activates the myrosinase and enables the hydrolysis of the glucoraphanin into sulforaphane. The hydrolysate thus obtained still contains lipids, which have to be eliminated, at least partially. One of these lipids is erucic acid or 13-docosenoic acid. Erucic acid is a fatty acid that is toxic to animals. It is therefore necessary to reduce its concentration to an acceptable level, i.e. below 5%. This reduction is obtained by treating the hydrolysate with acetone. This solvent also has high affinity with sulforaphane. It therefore makes it possible to continue the dilapidation of the hydrolyzed cake without loss of the active principle. In addition, the use of this solvent is permitted in the food and pharmaceutical industries.

Thus, a hydrolysate with a low content of lipids and erucic acid is obtained. The hydrolysate is then filtered and then dried to eliminate all the solid wastes and to recover a filtrate that is rid of acetone. The sulforaphane is then preferably extracted by the addition of ethyl acetate. Advantageously, ethyl acetate is added in a ratio of 1/1 to hydrolysate. This step eliminates the most polar molecules such as carbohydrates and polyphenols and certain proteins. Since the sulforaphane has average polarity, the use of this solvent preserves the totality of the sulforaphane present.

Then, a non-aqueous extract is obtained comprising 30% by weight of sulforaphane. This non-aqueous extract is then dried on a matrix of maltodextrin and gum *arabica* (E414). The drying of this resin gives a powder. The particles of this powder are then encapsulated with these same constituents, namely gum *arabica* and maltodextrin. This encapsulation stabilizes the sulforaphane molecules and gives a powder containing 10% of sulforaphane. Indeed, sulforaphane is an extremely unstable compound and, if it does not have such an encapsulation, it deteriorates very rapidly after being formed.

The method according to the invention therefore gives a stabilized sulforaphane-rich extract that can be stored in normal temperature and atmospheric conditions for the subsequent manufacture of nutraceutical or pharmaceutical compositions.

The encapsulation is done by means of any method known to those skilled in the art enabling a coating with maltodextrin or gum *arabica* (E414).

The encapsulated powder obtained through the method of the invention can then undergo an additional step of compression, according to any method well known to those skilled in the art, in order to obtain a tablet.

This tablet can then be coated according to any method well known to those skilled in the art, in order to form coated pills.

DESCRIPTION OF ONE EMBODIMENT ACCORDING TO THE INVENTION

The general principle of the invention relies on the regular administration of doses of sulforaphane in order to treat or prevent the recurrence of prostate cancer.

Using the method of the invention described here above, non-aqueous sulforaphane extract, stabilized by coating, was obtained in the form of an encapsulated powder containing 10% by weight of sulforaphane. This powder was compressed and then coated to give a composition according to the invention that takes the form of a coated pill.

In the context of the present embodiment, this composition in the form of a coated pill has the following composition:
  non-aqueous extract of broccoli Brassica Oleracea (var. *Italica*) seeds;
  dilutent: dibasic calcium phosphate, microcrystalline cellulose; anti-agglomerating agent: magnesium carbonate, silica, magnesium stearate;
  coating agent: lacquer gum, saccharose, titanium dioxide, polyvinyl pyrrolidone, beeswax, carnauba wax, talc;
  coloring agent: sucrose, titanium dioxide (E171), acacia gum (E414), brilliant blue FCF (E133), quinoleine yellow (E104), sodium benzoate (E211), indigotine (E132).

The efficacy of such a composition containing encapsulated sulforaphane and taking the form of a coated pill was tested.

In this context, 16 patients having undergone surgical resection of the prostate following a diagnosis of histologically proven adenocarcinoma of the prostate (Gleason score<7) were selected to participate in the study. These patients all showed biological recurrence defined by an increase in PSA levels of over 0.2 ng/ml and had therefore been treated with complementary external radiotherapy.

These patients received a dose of 30 mg per day orally for three months, i.e. namely three coated pills distributed through the day, each tablet containing 10 mg by weight of sulforaphane.

Each patient underwent an intensive clinical examination (blood tests, hemogram, weighing, etc).

The PSA of each patient was measured by taking blood samples at t=0, t=14 days, t=30 days, t=3 months. Samples were collected at t=4 months, t=5 months, i.e. respectively one month and two months after the treatment had ended in order to observe the progress of the PSA level at the end of the treatment.

The efficacy of the treatment was assessed through measurement of the PSA doubling time. This is defined as the number of months needed for a patient's PSA to double in value. This is a reliable indicator of the virulence and speed of development of a metastasis of the primitive prostate cancer.

For 20% of the patients, the PSA greatly diminished during treatment. This result suggests that the metastasis producing the PSA is in regression.

For 60% of the patients, the PSA doubling time lengthened during the treatment.

For 20% of the remaining patients, the PSA level doubling time continued to lengthen despite stoppage of the treatment.

More than half of these 80% of patients for whom the PSA level doubling time was lengthened showed a factor of increase of 50% and one third of them showed a factor of increase of over 200%.

It can therefore clearly be seen that a pharmaceutical composition according to the invention enables the efficacious slowing down of the PSA level doubling time This slowing down means that the growth of the tumor that causes the production of PSA is greatly slowed down. In addition, it is clearly worthwhile to be able to extend the patient's life and so enable him to have a better quality of life and to be able to take action when the tumor is still at a curable stage Given the results of this study, the composition according to the invention therefore makes it possible to:
  reduce the PSA, reflecting a regression of the tumor, or considerably slow down the progress of the tumor,
  Furthermore, none of the 16 patients showed any allergic reaction to the treatment.

In other embodiments, it is possible to use compositions containing more than 10% by weight of sulforaphane extract.

The invention claimed is:
1. A method for obtaining a sulforaphane-containing composition for the treatment of prostate cancer or its recurrence comprising:
  a. mechanically cold pressing non-sprouted broccoli seeds of the *Brassica Oleracea Italica* variety to obtain a partially delipidated cake containing glucoraphanin;
  b. obtaining a hydrolysate by enzymatically hydrolyzing the partially delipidated cake to hydrolyze the glucoraphanin into sulforaphane;

c. adding acetone to the hydrolysate to reduce lipid content and erucic acid content of the hydrolysate to a concentration below 5% by weight;
d. filtering the hydrolysate to recover a filtrate with a low content of lipids and a concentration below 5% by weight of erucic acid;
e. evaporating the acetone of the filtrate to recover an aqueous phase;
f. adding ethyl acetate to the aqueous phase to recover a phase containing the ethyl acetate and sulforaphane;
g. evaporating the ethyl acetate contained in the phase containing the ethyl acetate and sulforaphane to obtain a non-aqueous extract containing at least 30% by weight of sulforaphane;
h. drying the non-aqueous extract on a polysaccharide support selected from the group consisting of: acacia gum, maltodextrin, and their mixture, to obtain a powder;
i. incorporating the powder in a polysaccharide matrix selected from the group consisting of: acacia gum, maltodextrin, and the mixture thereof, to obtain an encapsulated powder containing at least 10% by weight of sulforaphane
j. incorporating the encapsulated powder within a pharmaceutical form selected from the group consisting of: a capsule, a tablet, a coated pill, and a film-coated tablet;
said method being performed without a step of aqueous extraction between the step g and the step h.

* * * * *